US008552372B2

United States Patent
Nojima

(10) Patent No.: US 8,552,372 B2
(45) Date of Patent: Oct. 8, 2013

(54) METHOD AND SYSTEM OF EVALUATING DISTRIBUTION OF LATTICE STRAIN ON CRYSTAL MATERIAL

(75) Inventor: Kazuhiro Nojima, Tokyo (JP)

(73) Assignee: Elpida Memory, Inc., Tokyo (JP)

( * ) Notice: Subject to any disclaimer, the term of this patent is extended or adjusted under 35 U.S.C. 154(b) by 0 days.

(21) Appl. No.: 13/475,408

(22) Filed: May 18, 2012

(65) Prior Publication Data

US 2012/0292504 A1  Nov. 22, 2012

(30) Foreign Application Priority Data

May 19, 2011  (JP) ................. 2011-112618

(51) Int. Cl.
*G01N 23/20* (2006.01)
*H01J 37/26* (2006.01)

(52) U.S. Cl.
USPC ............................ 250/307; 250/306; 250/311

(58) Field of Classification Search
USPC .............................. 250/306–311; 378/70–73
See application file for complete search history.

(56) References Cited

U.S. PATENT DOCUMENTS

| | | | | |
|---|---|---|---|---|
| 4,561,062 | A * | 12/1985 | Mitchell | 702/40 |
| 2006/0113473 | A1* | 6/2006 | Taniguchi et al. | 250/310 |
| 2007/0069128 | A1* | 3/2007 | Soeda | 250/311 |
| 2007/0096204 | A1 | 5/2007 | Shiratake | |
| 2011/0084209 | A1* | 4/2011 | Chung et al. | 250/311 |
| 2011/0220796 | A1* | 9/2011 | Nicolopoulos et al. | 250/307 |

FOREIGN PATENT DOCUMENTS

| | | |
|---|---|---|
| JP | 6-36729 A | 2/1994 |
| JP | 2004-093263 A | 3/2004 |
| JP | 2006-242914 A | 9/2006 |
| JP | 2007-123551 A | 5/2007 |

OTHER PUBLICATIONS

Usuda, et al. "Strain Characterization in Soi and Strained-Si on SGOI MOSFET Channel Using Nano-Beam Electron Diffraction (NBD)", Materials Science and Engineering B 124-125 (2005) 143-147.*
Usuda et al, "Strain Characterization in SOI and Strained-Si on SGOI MOSFET Channel Using Nano-Beam Electronics (NBD)", Materials Science and Engineering B 124-125 (2005) 143-147.*
N. Nakanishi et al., "Strain Mapping Technique for Performance Improvement of Strained MOS'FETs with Scanning Transmission Electron Microscopy", IEEE, 2008, pp. 431-434.
Koji Usuda et al, "Strain Characterization in SOI and Strained-Si on SGOI MOSFET Channel using Nano-Beam Electron Diffraction (NBD)", Materials Science and Engineering B, 2005, 143-147, vol. 124-125.

* cited by examiner

*Primary Examiner* — Robert Kim
*Assistant Examiner* — David E Smith
(74) *Attorney, Agent, or Firm* — Sughrue Mion, PLLC

(57) ABSTRACT

A crystal material lattice strain evaluation method includes illuminating a sample having a crystal structure with an electron beam in a zone axis direction, and selectively detecting a certain diffracted wave diffracted in a certain direction among a plurality of diffracted waves diffracted by the sample. The method further includes repeating the illuminating step and the selectively detecting step while scanning the sample, and obtaining a strain distribution image in a direction corresponding to the certain diffracted wave from diffraction intensity at each point of the sample.

18 Claims, 17 Drawing Sheets

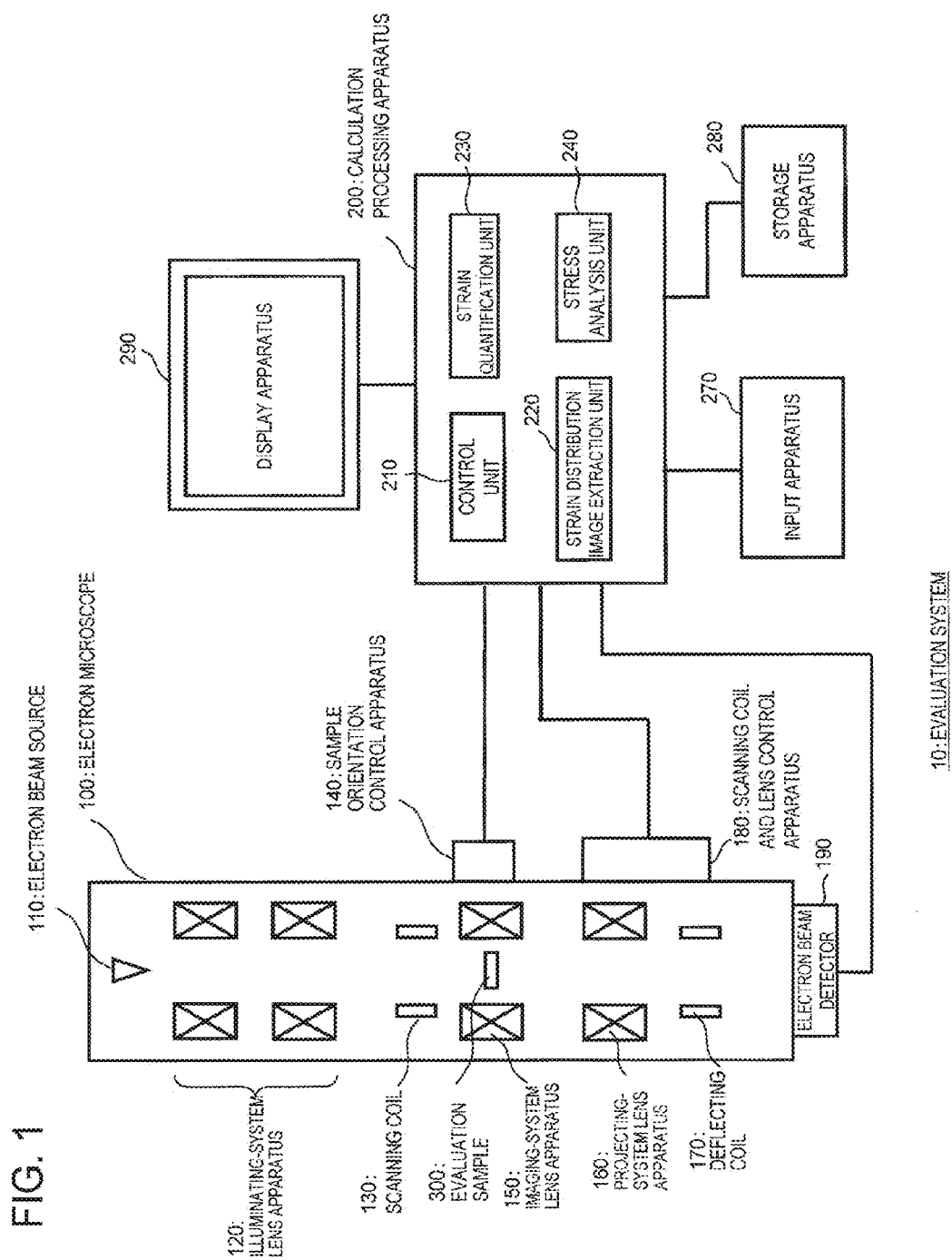

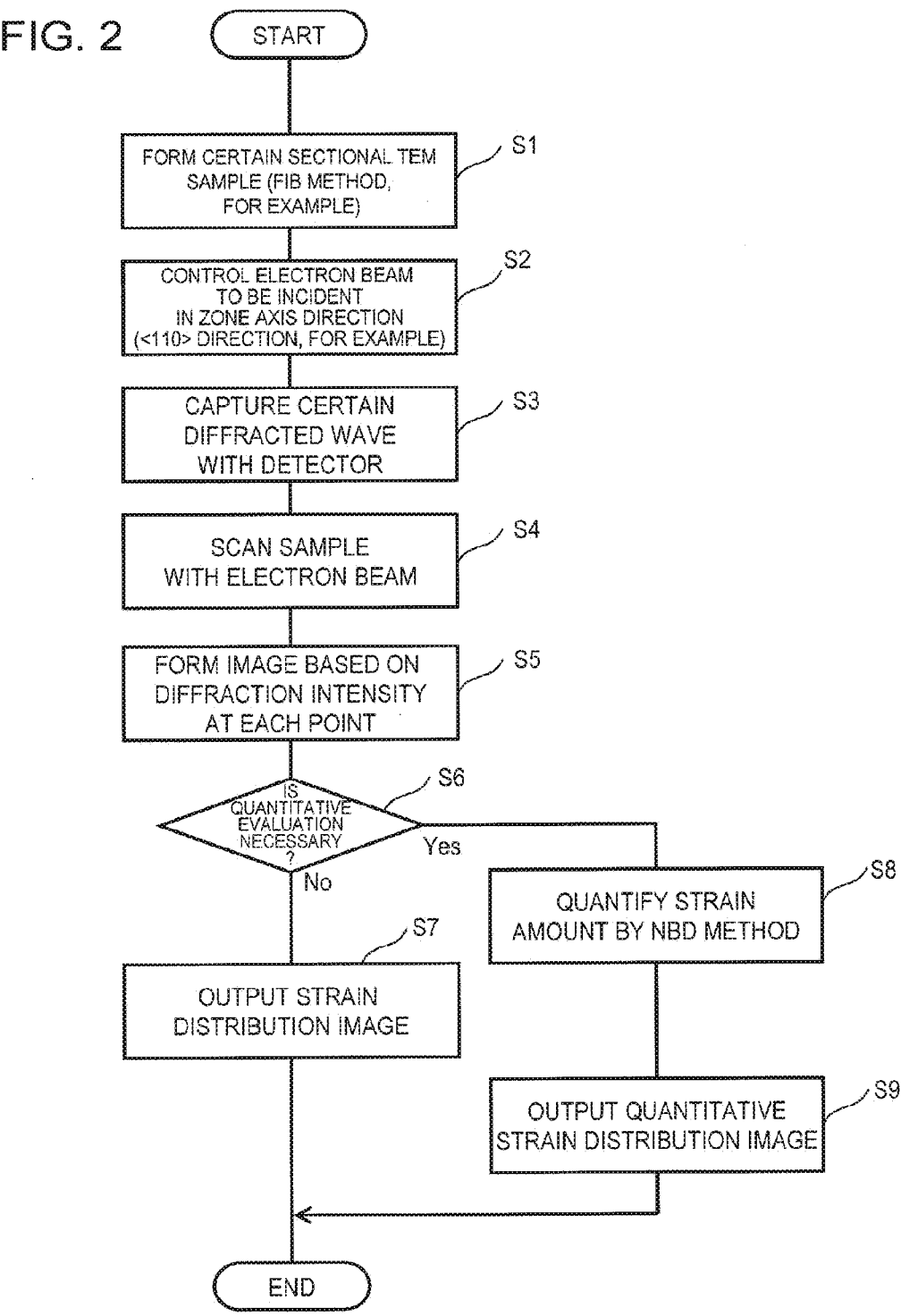

FIG.4A

RELATIONSHIP AMONG RECIPROCAL LATTICE POINT, EWALD SPHERE, AND EXCITATION ERROR Sg

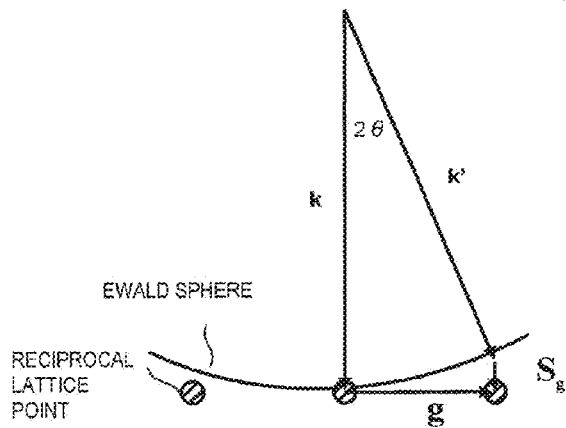

$$S_g \propto \frac{|\mathbf{g}|^2}{|\mathbf{k}|}$$

$$|\mathbf{g}| = \frac{1}{d_{hkl}} = \frac{\sqrt{h^2 + k^2 + l^2}}{a}$$

$$|\mathbf{k}| = \frac{1}{\lambda}$$

g : RECIPROCAL LATTICE VECTOR
k : WAVE VECTOR
d : LATTICE SPACING
a : LATTICE CONSTANT
h,k,l : LATTICE PLANE INDEX
λ : ELECTRON BEAM WAVELENGTH

FIG.4B

RELATIONSHIP BETWEEN RECIPROCAL LATTICE POINT AND EXCITATION ERROR WHEN LATTICE STRAIN IS CAUSED

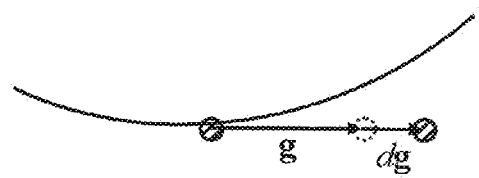

$$S_g \propto \frac{|\mathbf{g} + d\mathbf{g}|^2}{|\mathbf{k}|}$$

RECIPROCAL LATTICE POINT MOVING IN X DIRECTION

TARGET RECIPROCAL LATTICE POINT

STRESS CAUSED ON SAMPLE IN X DIRECTION

300

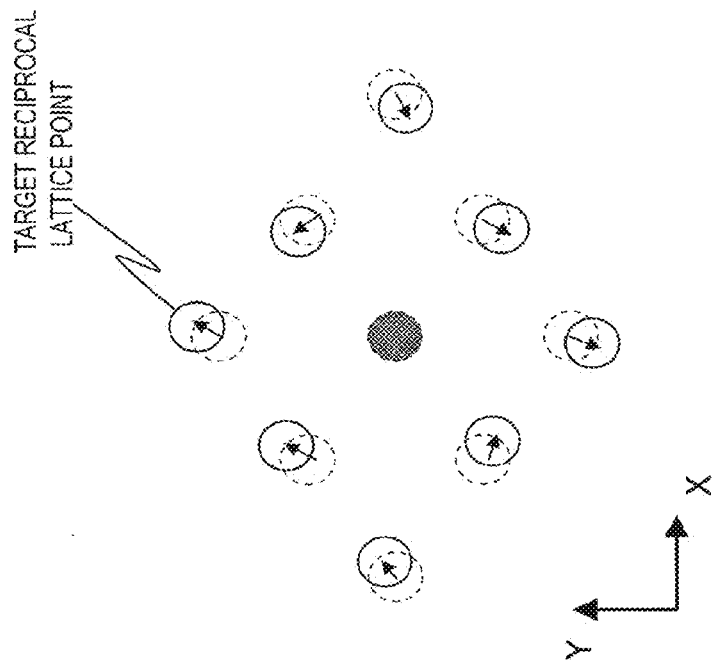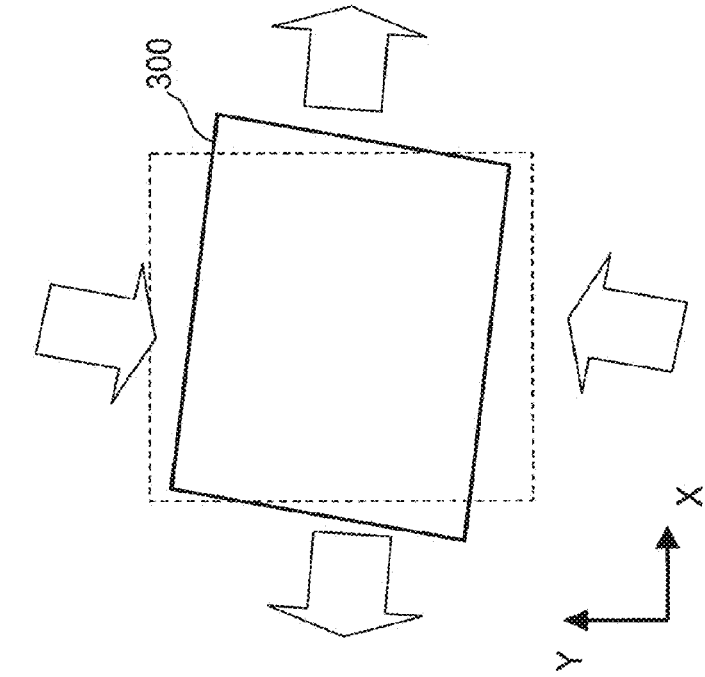
FIG.11A STRESS CAUSED ON SAMPLE IN COMPLEX DIRECTIONS
FIG.11B RECIPROCAL LATTICE POINT MOVING IN COMPLEX DIRECTIONS

LARGE CONVERGENT ANGLE

SMALL CONVERGENT ANGLE (BETTER PARALLELISM)

RECIPROCAL LATTICE POINT

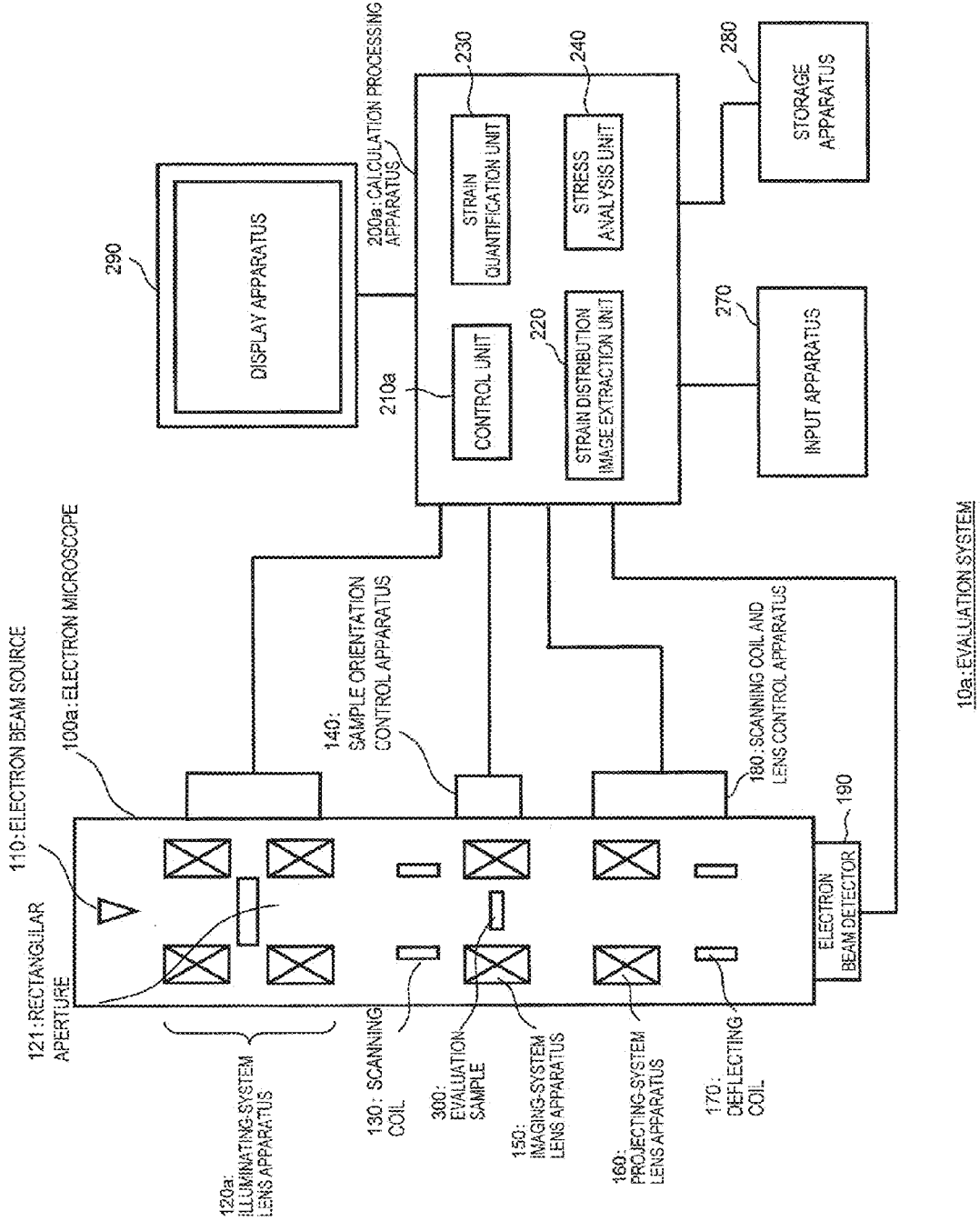

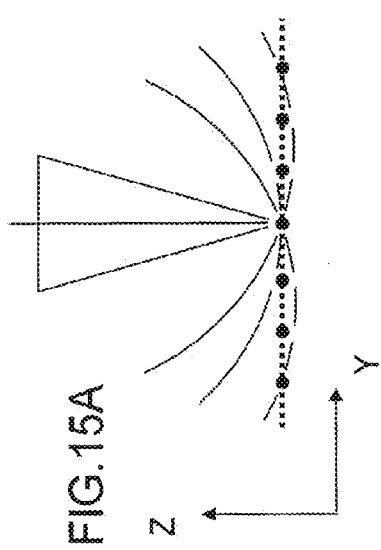
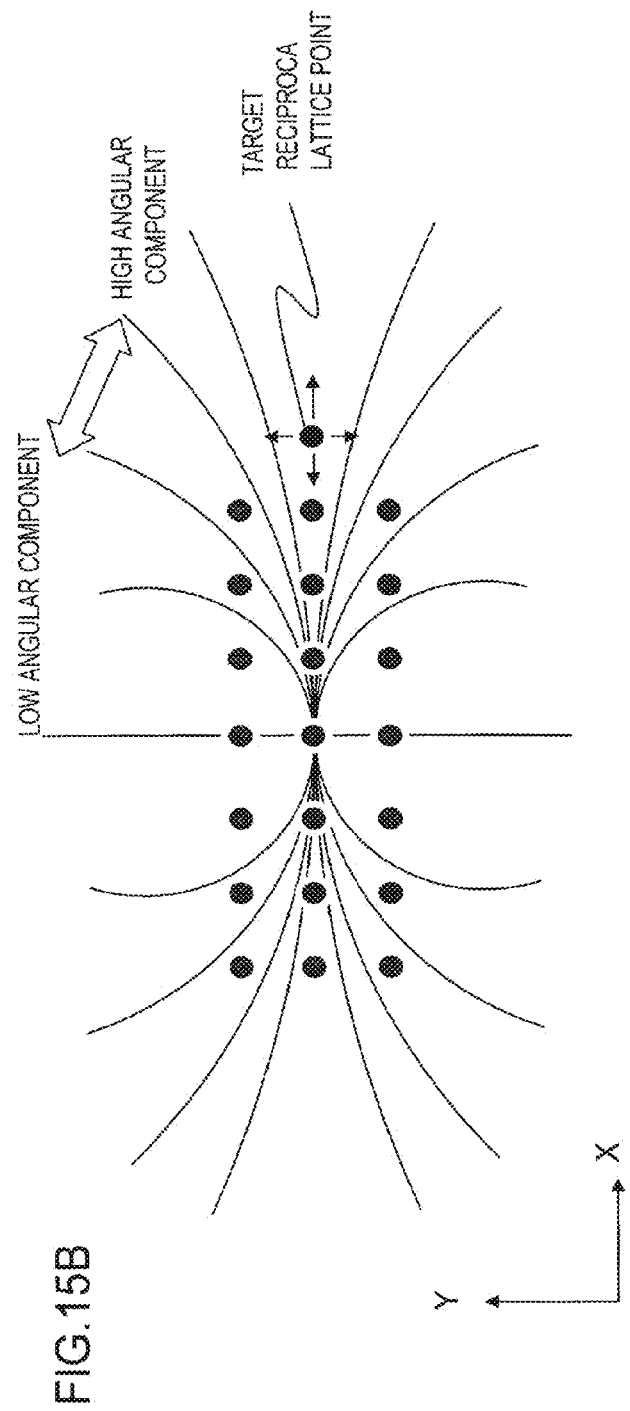
FIG. 15A
FIG. 15B

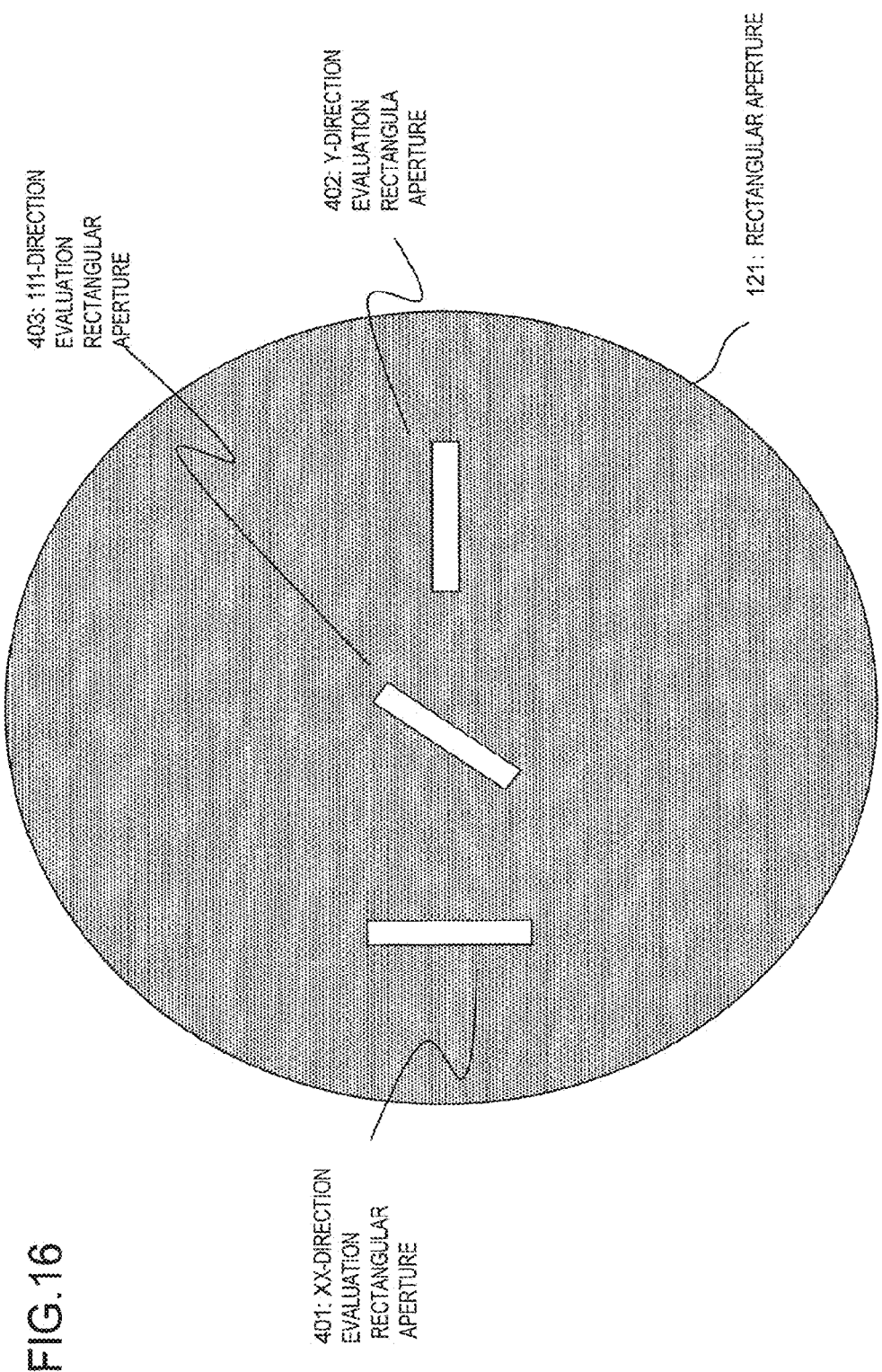

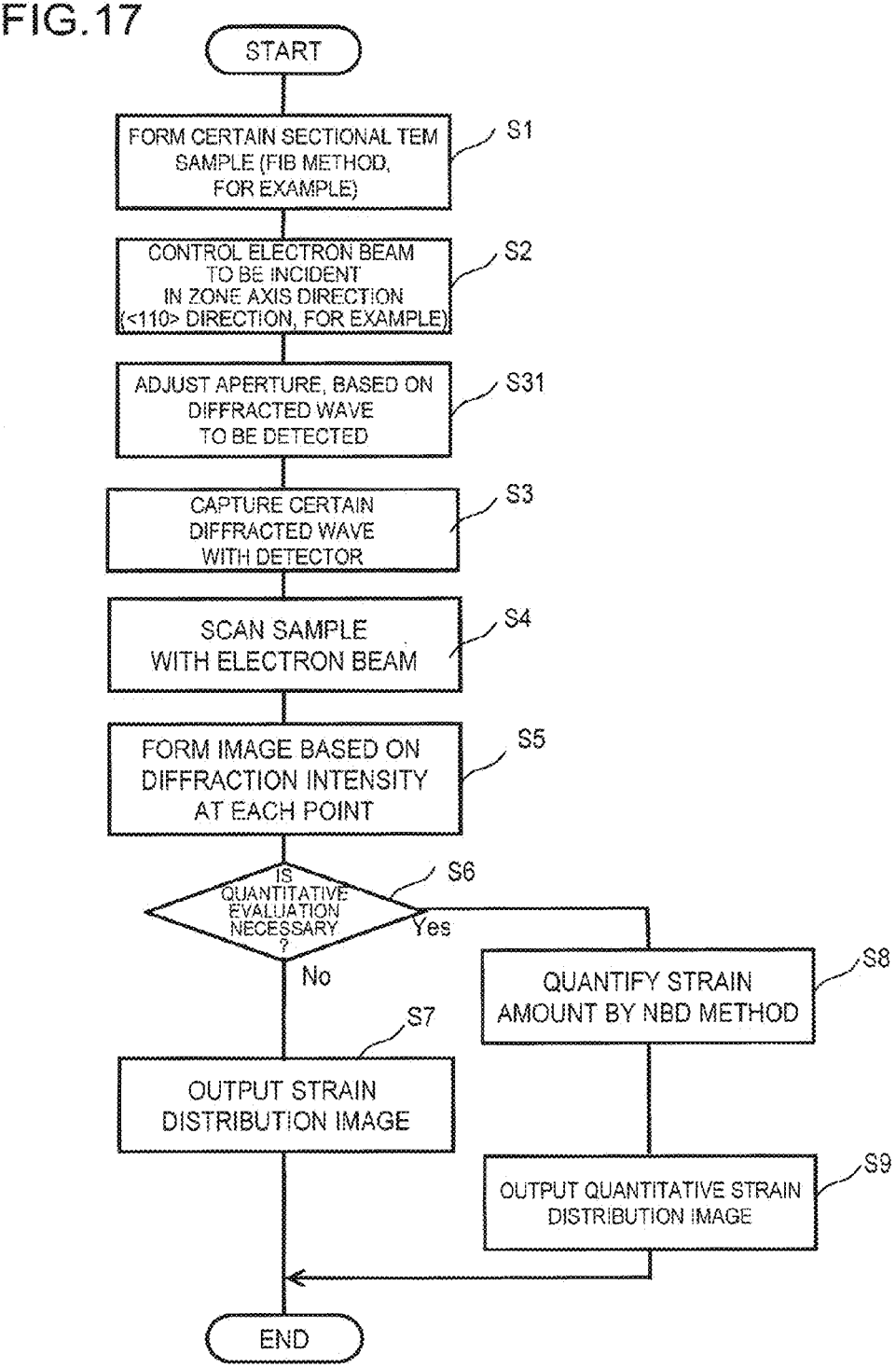

METHOD AND SYSTEM OF EVALUATING DISTRIBUTION OF LATTICE STRAIN ON CRYSTAL MATERIAL

TECHNICAL FIELD

Reference to Related Application

This application is based upon and claims the benefit of the priorities of Japanese patent application No. 2011-112618, filed on May 19, 2011 and Japanese patent application No. 2012-034676, filed on Feb. 21, 2012 the disclosure of which is incorporated herein in its entirety by reference thereto.

The present invention relates to a method and a system of evaluating a distribution of lattice strain on crystal material. In particular, it relates to a method and a system of evaluating a distribution of lattice strain on crystal material used in a semiconductor device or the like by using electron beam diffraction.

BACKGROUND

Description of the Related Art

When an LSI device is manufactured, stress generated by use of various types of material causes lattice strain on a crystal structure used in a semiconductor device. Such lattice strain is one of the important physical quantities that exhibit crystal material properties. The stress and lattice strain change, depending on the difference in mechanical physical properties of various types of material used in LSI device processes or depending on heat treatment used in processes. The lattice strain is a cause of a crystal defect or the like, resulting in device failure. In addition, in recent years, for example, attempts are being made to improve the electron and hole mobility of silicon, by using the lattice strain. Namely, attempts are being made to improve physical properties of crystal material by actively utilizing the lattice strain. Thus, if the lattice strain is utilized properly, improvement in device performance can be expected. However, if the lattice strain is not controlled properly, a crystal defect leading to device malfunction is caused. Therefore, evaluation of the stress and lattice strain on crystal material and optimization of process conditions are essential in the development of LSI devices.

Conventionally, the stress and lattice strain on crystal material such as in a semiconductor device have been evaluated by X-ray diffractometry, Raman spectroscopy, or the like. However, recent reduction in device size is making these conventional stress and lattice strain evaluation methods insufficient in spatial resolution, and it is becoming more difficult to obtain sufficient results. Therefore, a convergent-beam electron diffraction (CBED) method and a nano-beam electron diffraction (NBD) method are being proposed as methods using an electron beam and evaluating localized stress and lattice strain.

For example, Patent Document 1 discloses an apparatus and a method using the CBED method and evaluating strain on crystal material. In addition, Non-Patent Document 1 discloses using the NBD method and evaluating strain on an SOI MOSFET. In addition, Patent Documents 2 and 3 disclose a method of using a diffraction contrast and two-dimensionally evaluating lattice strain instantly. Non-Patent Document 2 discloses a strain evaluation method using thermal diffuse scattering electron intensity. Patent Document 4 discloses a semiconductor device having a trench-gate transistor as an example of a minute device structure requiring localized stress and lattice strain evaluation.

Patent Document 1:
Japanese Patent Kokai Publication No. JP-H06-36729A
Patent Document 2:
Japanese Patent Kokai Publication No. JP2004-93263A
Patent Document 3:
Japanese Patent Kokai Publication No. JP2006-242914A
Patent Document 4:
Japanese Patent Kokai Publication No. JP2007-123551A, which corresponds to US Patent Application Publication No. US2007/0096204A1.
Non-Patent Document 1:
K. Usuda et al., "Strain characterization in SOI and strained-Si on SGOI MOSFET channel using nano-beam electron diffraction (NBD)", Materials Science and Engineering B124-125 (2005), p. 143 to 147.
Non-Patent Document 2:
N. Nakanishi et al., "Strain Mapping Technique for Performance Improvement of Strained MOSFETs with Scanning Transmission Electron Microscopy", IEDM2008, p. 431 to 434.

SUMMARY

The disclosure of the above Patent Documents and Non-patent Documents are incorporated herein in their entirety by reference thereto. The following analysis is given by the present invention. Since the above CBED and NBD methods are used for evaluation on one-dimensional points, it is insufficient to discuss the influence caused by lattice strain on device characteristics. Even with such evaluation method based on the CBED and NBD methods, in principle, it is possible to set many evaluation points and obtain a two-dimensional distribution. However, since the analysis method requires complicated and time-consuming operations, such method is not effective. In addition, these evaluation methods are not established as evaluation apparatuses. The evaluation methods are merely known as application examples of a transmission electron microscope. Namely, skilled techniques are required to obtain reliable results.

In addition, based on the evaluation methods disclosed in Patent Documents 2 and 3 and Non-Patent Document 2, lattice strain in a variety of directions is added and measured, it is insufficient to discuss the influence caused by lattice strain in a current direction. Generally, LSI devices are planarly formed on a silicon semiconductor wafer or the like and are designed so that current flows in one direction. Thus, to discuss the influence caused by strain on device characteristics, it is necessary to evaluate strain, in view of directional components, such as a strain distribution, principal strain, and shear lattice strain in each of various directions.

According to a first aspect of the present invention, there is provided a method of evaluating a distribution of lattice strain on crystal material. The method comprises illuminating a sample having a crystal structure with an electron beam in a zone axis direction (termed "illuminating step"), and selectively detecting a certain diffracted wave diffracted in a certain direction among a plurality of diffracted waves diffracted by the sample (termed "selectively detecting step"). The method further comprises repeating the illuminating step and the selectively detecting step while scanning the sample, and obtaining a strain distribution image in a direction corresponding to the certain diffracted wave from diffraction intensity at each point of the sample.

According to a second aspect of the present invention, there is provided a system of evaluating a distribution of lattice strain on crystal material. The system comprises a scanning transmission electron microscope that illuminates a sample with an electron beam, scans the sample, and detects a diffracted wave transmitted or diffracted by the sample. The system further comprises a strain distribution image extraction unit that selects a certain diffracted wave among diffracted waves transmitted or diffracted by the sample and obtains a strain distribution image.

According to a third aspect of the present invention, there is provided a non-transitory computer-readable recording medium storing a computer program used in an evaluation system. The evaluation system comprises a scanning transmission electron microscope and a computer that controls the scanning transmission electron microscope and processes measurement data obtained by the scanning transmission electron microscope.

The computer program causes the computer to execute processes of: controlling the scanning transmission electron microscope so that a sample having a crystal structure is illuminated with an electron beam and a diffracted wave transmitted or diffracted by the sample is detected; and scanning the sample, selecting a certain diffracted wave among diffracted waves transmitted or diffracted by the sample, and obtaining a strain distribution image.

BRIEF DESCRIPTION OF THE DRAWINGS

FIG. 1 is a block diagram illustrating an overall configuration of a system of evaluating a distribution of lattice strain on crystal material according to an exemplary embodiment of the present disclosure.

FIG. 2 is a flow chart illustrating a method of evaluating a distribution of lattice strain on crystal material according to an exemplary embodiment of the present disclosure.

FIGS. 4A and 4B illustrate a principle of obtaining a strain distribution image from a diffraction image of a certain diffracted wave: FIG. 4A illustrates a relationship among a reciprocal lattice point, an Ewald sphere, and an excitation error; and FIG. 4B illustrates the relationship between a reciprocal lattice point and an excitation error when lattice strain is caused.

FIG. 11A illustrates the direction in which stress is caused and FIG. 11B illustrates the direction in which a reciprocal lattice point is moved when complex stress is caused on a sample.

FIG. 13 is a block diagram illustrating an overall configuration of a system of evaluating a distribution of lattice strain on crystal material according to a fourth exemplary embodiment.

FIG. 15A illustrates the relationship between a cross section (YZ cross-section) of the electron beam incident in the longitudinal direction of the rectangular aperture and reciprocal lattice points and FIG. 15B illustrates the relationship between a cross section (XY cross-section) of the electron beam and the reciprocal lattice points according to the fourth exemplary embodiment.

FIG. 16 is a plan view illustrating another rectangular aperture according to the fourth exemplary embodiment.

FIG. 17 is a flow chart illustrating a method of evaluating a distribution of lattice strain on crystal material according to the fourth exemplary embodiment.

PREFERRED MODES

Exemplary Embodiments

Figure 3A:
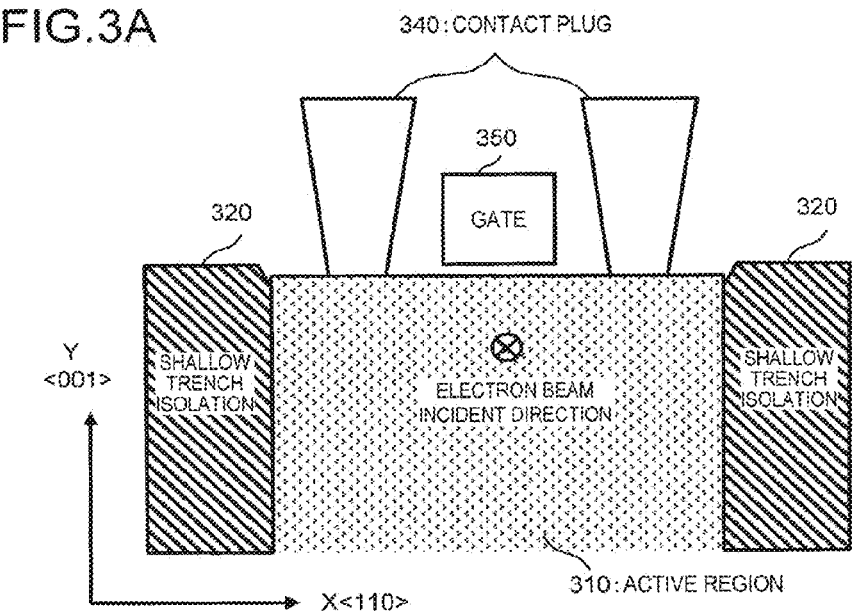
FIG. 3A illustrates the direction in which an electron beam is incident on crystal of a semiconductor device as an evaluation sample and FIG. 3B illustrates directions of diffracted waves.
Figure 3B:
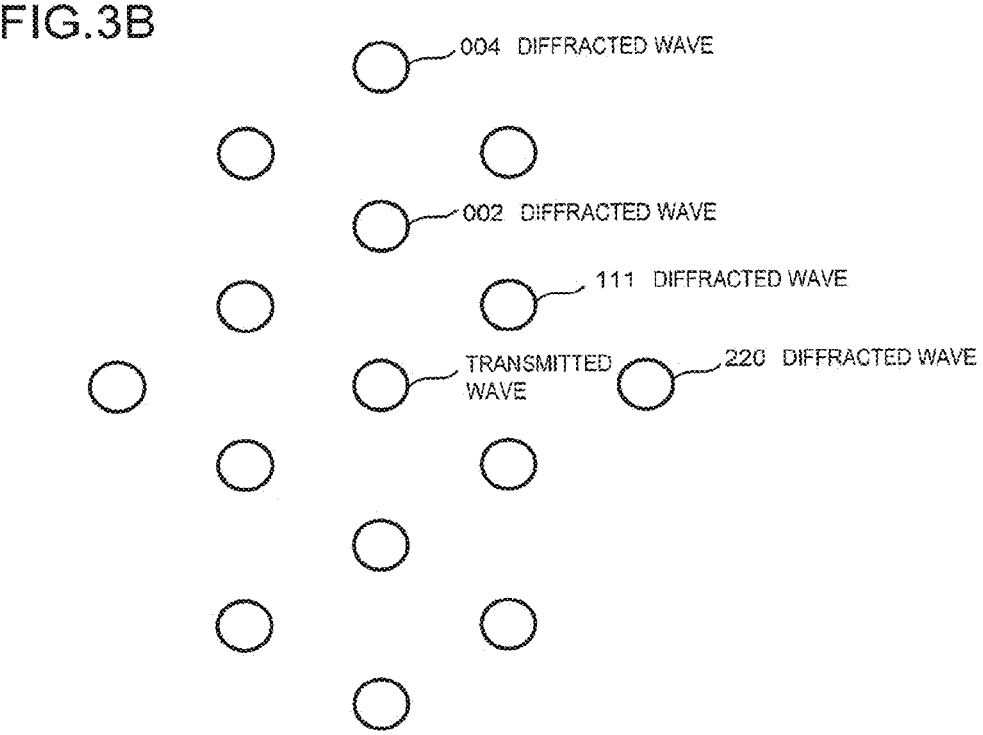

A summary of an exemplary embodiment of the present disclosure will be described. For example, by using a scanning transmission electron microscope as illustrated FIG. 1, if an electron beam is emitted to be incident on a thin semiconductor device sample as illustrated in FIG. 3A, a transmitted wave and diffracted waves as illustrated in FIG. 3B can be observed. As illustrated in FIGS. 5A to 5C and FIGS. 5D to 5F, from diffracted waves diffracted in different directions, a crystal strain distribution image corresponding to each of the diffraction directions can be obtained. In addition, by using a known method such as the NBD method to quantify strain distribution images, a shear strain distribution and a principal strain distribution can be grasped from quantified strain distribution images in a plurality of directions. Thus, a cause of strain can be determined, and the possibility of occurrence of a crystal defect can be predicted. The drawings referred to by way of symbols in this summary are merely used as examples to facilitate understanding of the present disclosure. Therefore, the present invention is not limited by the modes illustrated by the drawings.

Next, each of the exemplary embodiments will be described in detail with reference to the drawings.

First Exemplary Embodiment

FIG. 1 is a block diagram illustrating an overall configuration of a system 10 of evaluating a distribution of lattice strain on crystal material according to a first exemplary embodiment. The evaluation system 10 in FIG. 1 includes: a scanning transmission electron microscope 100; and a calculation processing apparatus 200 controlling the electron microscope 100 and processing measurement data obtained by the electron microscope 100.

The electron microscope 100 includes an electron beam source 110 outputting an electron beam used for observing an evaluation sample 300; an illuminating-system lens apparatus 120 using the electron beam outputted from the electron beam source 110 to illuminate the evaluation sample 300; and an imaging-system lens apparatus 150 functioning as an objective lens focusing an electron beam on a minute spot region of the evaluation sample 300. An electron beam transmitted by the evaluation sample 300 or an electron beam diffracted in the forward direction by the evaluation sample 300 is focused on an electron beam detector 190 by a projecting-system lens apparatus 160.

In addition, the electron microscope 100 includes a scanning coil 130 causing the electron beam emitted from the electron beam source 110 to scan the evaluation sample 300. The scanning coil 130 controls the electron beam to scan the evaluation sample 300. In addition, the electron microscope 100 includes a deflecting coil 170 selecting a certain one of the electron beams transmitted by the evaluation sample 300 or diffracted in the forward direction by the evaluation sample 300 and focusing the certain electron beam on the electron beam detector 190. In addition, the electron microscope 100 includes a scanning coil and lens control apparatus 180 controlling the scanning coil 130, the illuminating-system lens apparatus 120, the imaging-system lens apparatus 150, the projecting-system lens apparatus 160, and the deflecting coil 170.

In addition, the electron microscope 100 includes a sample orientation control apparatus 140 controlling the orientation of the evaluation sample 300, to align the crystal axis direction of the evaluation sample 300 with the electron beam illumination direction. The sample orientation control apparatus 140 executes fine-tuning of the direction of the evaluation sample 300, to align the crystal axis direction of the evaluation sample 300 with the electron beam illumination direction.

The sample orientation control apparatus 140 and the scanning coil and lens control apparatus 180 are connected to the calculation processing apparatus 200 and are controlled by a control unit 210 of the calculation processing apparatus 200. The electron beam detector 190 is also connected to the calculation processing apparatus 200 processing measurement data detected by the electron beam detector 190.

The calculation processing apparatus 200 is connected to an input apparatus 270, a storage apparatus 280, and a display apparatus 290. The input apparatus 270 includes an operation interface such as a keyboard and a mouse, so that an operator can control an overall operation of the evaluation system 10. The storage apparatus 280 can store programs for controlling measurement data and an overall operation of the evaluation system 10 and for analyzing measurement data. The display apparatus 290 can display measurement data detected by the electron beam detector 190 as image data and can display results obtained by evaluation and analysis executed by the calculation processing apparatus 200.

The calculation processing apparatus 200 includes, as incorporated functions, the control unit 210 controlling operations of the electron microscope 100, a strain distribution image extraction unit 221 extracting a strain distribution image from data detected by the electron beam detector 190, a strain quantification unit 230 using the NBD method or the like to quantify the magnitude of lattice strain based on a diffraction image position observed by the electron beam detector 190, and a stress analysis unit 240 analyzing stress caused on each of the regions of the evaluation sample 300 based on quantified strain distribution images in a plurality of directions or the like.

FIG. 2 is a flow chart illustrating a method of evaluating a distribution of lattice strain on crystal material. Next, a method of evaluating lattice strain on a semiconductor device will be described with reference to FIG. 2. First, in step S1 in FIG. 2, an FIB (Focused Ion Beam) method or the like is used to form a sectional TEM (Transmission Electron Microscope) sample of a semiconductor device having a uniform thickness. In this step, when the sample is formed, it is desirable that the sample should be adjusted to have a thickness of 200 nm or less and that the sample should not have different structural distributions in the thickness direction in accordance with dimensions of the semiconductor device as much as possible (namely, it is desirable that the sample should be formed to have an uniform structure in the thickness direction).

FIG. 3A illustrates an evaluation sample of a semiconductor device. The semiconductor device in FIG. 3A is a semiconductor device on which a general silicon-crystal MOSFET is formed. As illustrated in FIG. 3A, the sectional TEM sample of the semiconductor device is formed so that the X-axis and Y-axis directions of the single-crystal silicon of an active region 310 are <110> and <001>, respectively. The active region 310 is formed in the middle of the semiconductor device in the X-axis direction, and a shallow trench isolation 320 is formed on either side of the active region 310 in the X-axis direction. In addition, a gate 350 is formed on the surface of the semiconductor device (positive direction in the Y-axis direction), and a contact plug 340 connected to the active region 310 is formed on either side of the gate 350 in the X-axis direction.

Next, the sample formed in step S1 is placed at a position corresponding to the position of the evaluation sample 300 in the (scanning transmission) electron microscope 100 of the evaluation system 10 in FIG. 1. In addition, the sample orientation control apparatus 140 is used to control the orientation of the evaluation sample 300 so that the electron beam is incident on the evaluation sample 300 along the zone axis thereof (step S2 in FIG. 2). In this example, the zone axis along which the electron beam is incident is set to be in the Si <110> direction. In FIG. 3A, the X-axis and the zone axis directions in which the electron beam is incident are perpendicular to each other. In view of the crystalline symmetry, both the directions are denoted by <110>. Namely, in FIG. 3A, the sample orientation control apparatus 140 controls the orientation of the evaluation sample 300 so that the electron beam is incident in the direction perpendicular to both of the X-axis and the Y-axis.

Next, the deflecting coil 170 is adjusted so that a certain diffracted wave is captured by the electron beam detector 190 among an electronic diffraction pattern which is formed downstream of the evaluation sample 300 (in the traveling direction of the electron beam) when the electron beam is focused on the evaluation sample 300 (step S3 in FIG. 2). Namely, if the electron beam is emitted to be incident on the evaluation sample 300 in the direction perpendicular to the X-axis <110> and the Y-axis <001> in FIG. 3A, a transmitted wave and a plurality of diffracted waves such as diffracted waves 002, 004, 111, and 220 are focused near the electron beam detector 190 located downstream of the evaluation sample 300 (in the traveling direction of the electron beam), as illustrated in FIG. 3B. The crystal plane of the active region 310 and the diffracted waves correspond to each other. For example, in step S3, the deflecting coil 170 is controlled so that the electron beam detector 190 captures the diffracted wave 220 when lattice strain in the X direction is evaluated and the diffracted wave 004 or 002 when lattice strain in the Y direction is evaluated. Thus, among the transmitted wave and the diffracted waves, only a certain diffracted wave is captured by the electron beam detector 190.

While the deflecting coil 170 is fixed so that only a certain diffracted wave is captured by the electron beam detector 190, the scanning coil 130 is controlled to cause the electron beam to scan the evaluation sample 300. Consequently, a contrast image corresponding to a strain distribution in a certain direction (the X <110> direction or the Y <001> direction in FIG. 3A) can be obtained (in steps S4 and S5 in FIG. 2).

Figure 6A:
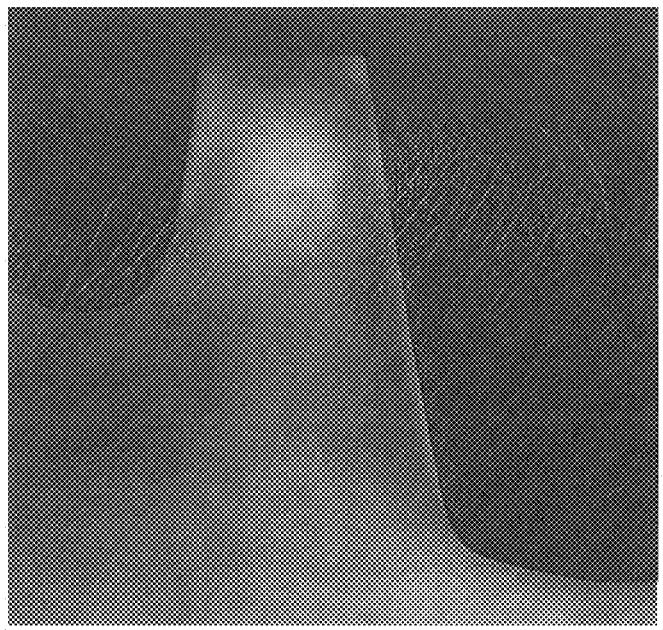
FIG. 6A illustrates a diffracted wave intensity image.
Figure 6B:
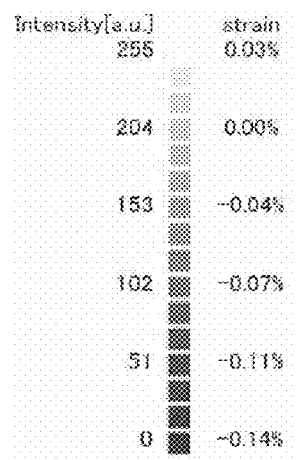
FIG. 6B illustrates a conversion scale between the diffracted wave intensity and the lattice strain magnitude.
Figure 6C:
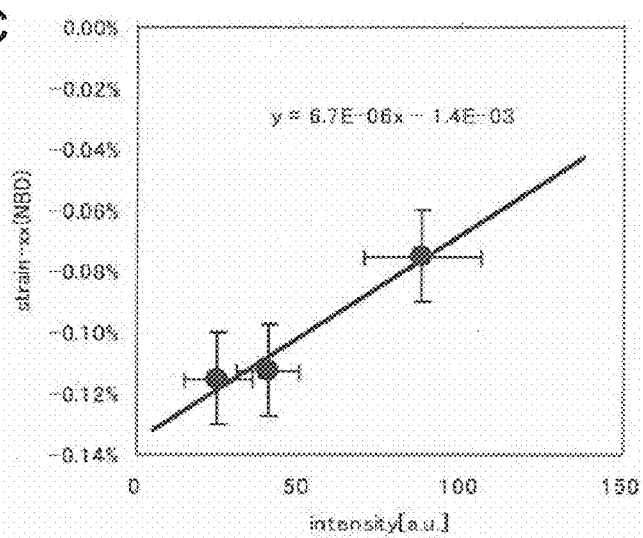
FIG. 6C illustrates a calibration curve of the diffracted wave intensity and the lattice strain obtained by the NBD method.

If no quantitative evaluation is necessary for the lattice strain (No in step S6), a strain distribution image in each direction is acquired and the process is ended (step S7). If a quantitative evaluation is necessary for the lattice strain (Yes in step S6), the strain amount is quantified by the NBD method or the like and a quantitative strain distribution image is acquired (in steps S8 and S9). For example, as illustrated in FIG. 6C, the NBD method can be used to measure a few points of diffracted wave intensity and lattice strain, and the measurement values can be processed by linear regression to obtain a calibration curve. Based on this calibration curve, by displaying a conversion scale between the diffracted wave intensity and the lattice strain magnitude as illustrated in FIG. 6B along with a diffracted wave intensity image as illustrated in FIG. 6A, a quantified strain distribution in a certain direction can be displayed.

In FIG. 3A, the TEM sample is formed so that the zone axis in the electron beam incident direction is set to be in the Si <110> direction. However, even if the zone axis in the electron beam incident direction may be set in the Si <100> direction, a strain distribution based on a diffracted wave can be evaluated. Namely, a strain distribution in an arbitrary crystal axis direction can be evaluated.

Next, a principle of acquiring a contrast image corresponding to strain in accordance with the above method will be described with reference to FIGS. 4A and 4B. FIG. 4A illustrates reciprocal lattice points, an incident electron beam, and an Ewald sphere in a reciprocal lattice space. Based on Bragg's law, an electron beam incident on crystal is diffracted from the incident angle by 2θ. The intensity is determined by an excitation error Sg, which is the distance between a reciprocal lattice point and the Ewald sphere illustrated in FIG. 4A. The excitation error Sg is represented by expression 1, assuming that g represents a reciprocal lattice vector, k: a wave vector, d: lattice spacing, a: a lattice constant, h,k,l: a lattice plane index, and λ: an electron beam wavelength.

$$S_g \propto \frac{|g|^2}{|k|} \quad \text{[expression 1]}$$

$$|g| = \frac{1}{d_{hkl}} = \frac{\sqrt{h^2 + k^2 + l^2}}{a}$$

$$|k| = \frac{1}{\lambda}$$

If stress is caused on the crystal material and if the lattice strain is caused, a reciprocal lattice point is moved horizontally as illustrated in FIG. 4B. Accordingly, if the reciprocal lattice point is moved, since the excitation error Sg is changed, the diffraction intensity is also changed. The excitation error Sg when the reciprocal lattice point is moved can be represented by expression 2.

$$S_g \propto \frac{|g + dg|^2}{|k|} \quad \text{[expression 2]}$$

The electron beam wavelength used by a general electron microscope is approximately 0.0197 [Å] (when the acceleration voltage is 300 kV). Since the lattice strain evaluated with respect to the Ewald sphere radius given by the reciprocal of the wavelength is approximately a few % at most, the relationship between the excitation error Sg and the lattice strain can suitably be expressed by straight-line approximation. In addition, while there is an extinction distance ξg as a factor affecting the diffraction intensity, this is a parameter that is mainly dependent on the sample thickness and that is changed depending on the sample thickness or incident intensity. In the present exemplary embodiment, a sample having a sufficiently uniform thickness can be formed by the FIB method and the sample can be scanned in a constant incident direction. Thus, the diffraction intensity is not affected.

Since a minute device having a complex structure has a complex lattice strain distribution, use of the NBD method or the CBED method requires much time for detailed evaluation of a strain distribution. However, by using the method according to the first exemplary embodiment, a strain distribution image can be acquired instantly.

Second Exemplary Embodiment

Figure 7:
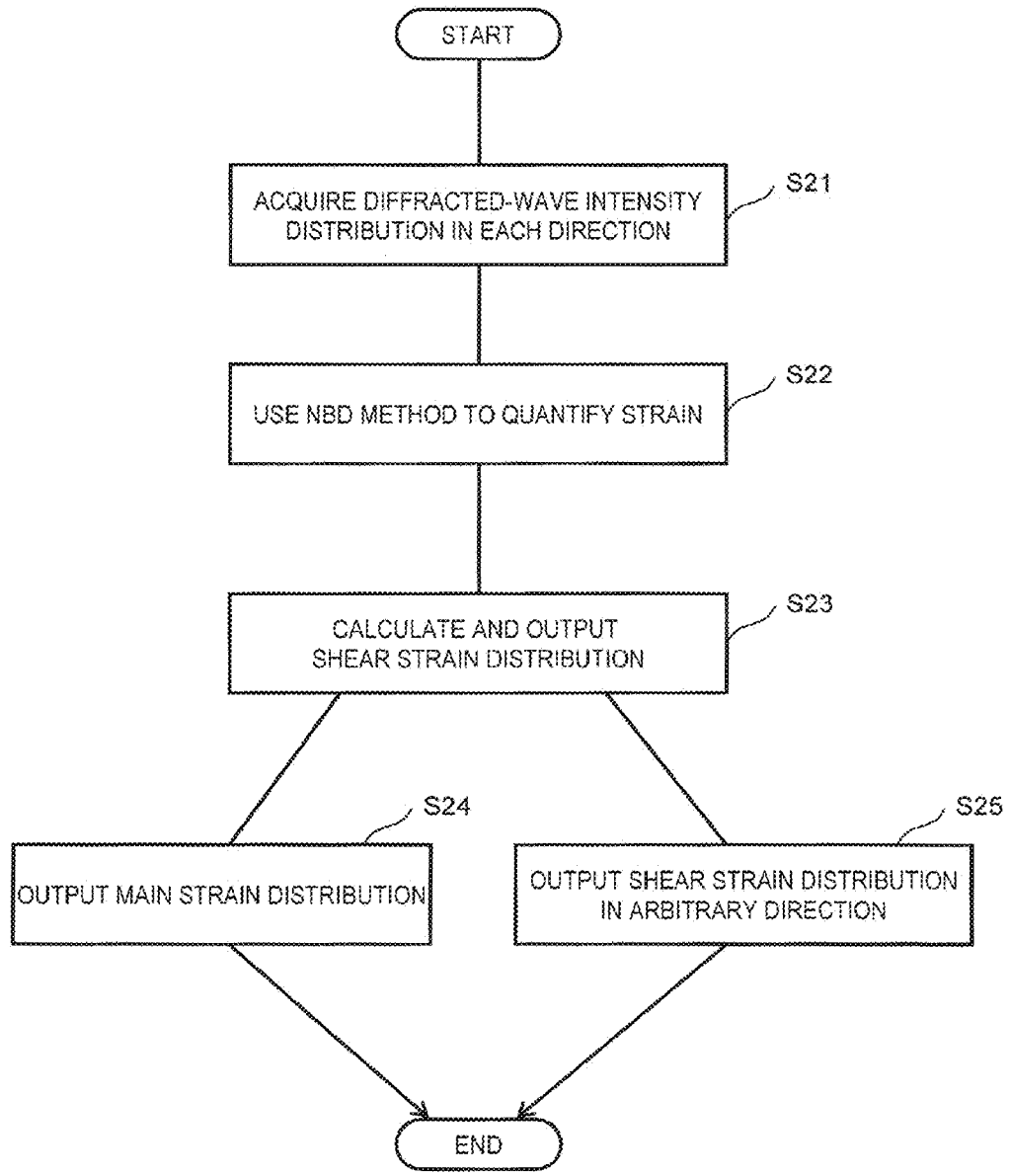
FIG. 7 is a flow chart illustrating a method of analyzing lattice strain from a lattice strain distribution.

In the first exemplary embodiment, outputting a quantitative strain distribution image in each direction is described. In a second exemplary embodiment, based on the output results according to the first exemplary embodiment, a principal strain distribution and a shear strain distribution in an arbitrary direction are outputted to grasp the cause of crystal strain and to predict the possibility of occurrence of a crystal defect. FIG. 7 is a flow chart illustrating a process procedure according to the second exemplary embodiment.

Figure 8C:
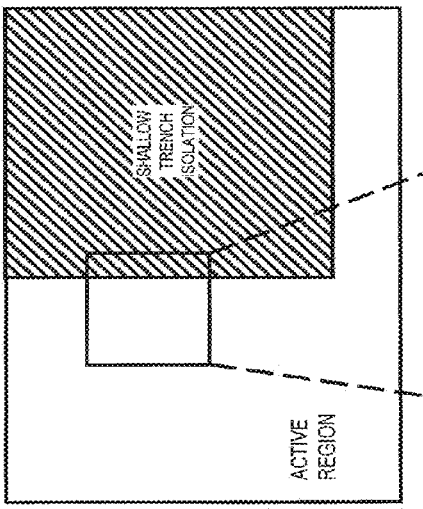
FIG. 8C is a plan view when an STI interface is formed with a taper angle with respect to the crystal axis.
Figure 8D:
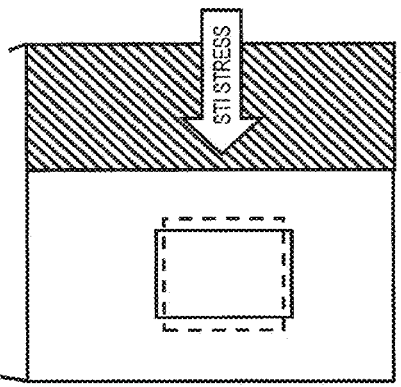
FIG. 8D is an enlarged view illustrating the stress direction.
Figure 8A:
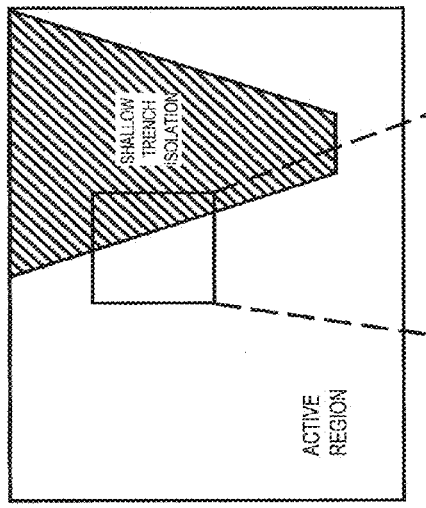
FIG. 8A is a plan view when an STI interface is formed perpendicular to the crystal axis of an active region.
Figure 8B:
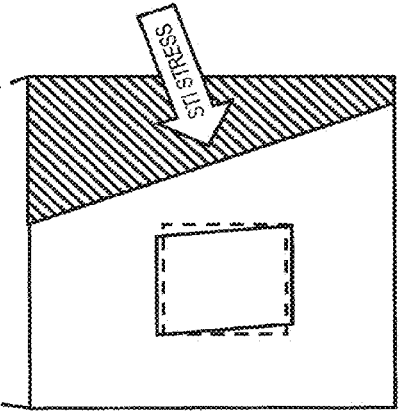
FIG. 8B is an enlarged view illustrating the stress direction.

Before the second exemplary embodiment is described, evaluation examples of lattice strain caused when a shallow trench isolation (STI) generally used in a silicon LSI device causes stress to an active region will be described with reference to FIGS. 8A to 8D. FIG. 8A is a plan view when an STI interface is formed in alignment with the crystal orientation in an active region. FIG. 8B is an enlarged view of a portion near the interface. FIG. 8C is a plan view when an STI interface is formed with a taper angle with respect to the crystal structure in an active region. FIG. 8D is an enlarged view of a portion near the interface.

As illustrated in FIGS. 8A and 8B, if an STI interface is formed in alignment with the crystal orientation in an active region, generally, stress is caused on the crystal structure in the active region in the directions perpendicular thereto. However, as illustrated in FIGS. 8C and 8D, if an STI interface is formed with a taper angle with respect to the crystal structure in an active region, the active region is subjected to not only the strain in the X and Y directions but also shear strain in the X and Y directions. It is known that such shear strain in a semiconductor device is a cause of a crystal defect. Thus, it is necessary that a manufacturing or design process should be controlled so that such shear strain does not cause a crystal defect.

However, by evaluating strain only in the X and Y directions, such shear strain cannot be determined. In addition, since strain in a direction perpendicular to an STI interface exhibits a maximum level, if the direction of a principal strain, which is the strain exhibiting a maximum level, can be determined, a stress source causing the strain can be determined, making it easier to provide feedback to the semiconductor manufacturing process. Next, an analysis method according to the second exemplary embodiment will be described. This method analyzes shear strain and principal strain, based on lattice strain distribution images in different directions obtained under different imaging conditions according to the first exemplary embodiment.

In the second exemplary embodiment, as in the first exemplary embodiment, a TEM sample formed by the FIB method is used. Thus, the stress component in the sample depth direction (in the direction that the electron beam is transmitted) is set to be zero through stress relaxation during the FIB processing. Consequently, two-dimensional stress approximation is possible. Hereinafter, lattice strain in a two-dimensional stress state will be described.

In FIG. 3B, strain distributions ($\epsilon_{xx}$), and ($\epsilon_{yy}$), and ($\epsilon_\theta$, $\theta$=35.3 degrees) in the X direction, the Y direction, and the 35.3-degree direction can be obtained based on intensity distribution images obtained by using the diffracted waves 220, 004, and 111, respectively (step S21 in FIG. 7). After each of the strain distribution images are acquired, the NBD method is used to quantify the diffracted wave intensity (step S22 in FIG. 7). For example, three particular points among the strain distribution images are measured by the NBD method to execute strain quantification of the diffraction intensity. As described above, the diffraction intensity and strain amounts can be suitably expressed by straight-line approximation.

Next, shear strain is calculated based on the strain distributions in the three directions (X, Y, and $\theta$ (35.3-degree) directions) (step S23 in FIG. 7). Shear strain $\gamma_{xy}$ can be acquired by expression 3 in which the X-, Y-, and $\theta$-direction strains are denoted by $\epsilon_{xx}$, $\epsilon_{yy}$, and $\epsilon_\theta$, respectively.

$$\gamma_{xy} = \frac{\varepsilon_\theta - (\varepsilon_{xx}\cos^2\theta + \varepsilon_{yy}\sin^2\theta)}{\cos\theta\sin\theta} \quad \text{[expression 3]}$$
$$\theta = 35.3°$$

In addition, expression 4 is obtained by transforming expression 3. Namely, the strain $\epsilon_\theta$ can be calculated by using the measured strain $\epsilon_{xx}$ and $\epsilon_{yy}$ and the calculated shear strain $\gamma_{xy}$.

$$\varepsilon_\theta = \frac{\varepsilon_{xx}+\varepsilon_{yy}}{2} + \frac{\varepsilon_{xx}-\varepsilon_{yy}}{2}\cos2\theta + \frac{1}{\gamma_{xy}}\sin2\theta \quad \text{[expression 4]}$$

Figure 9A:
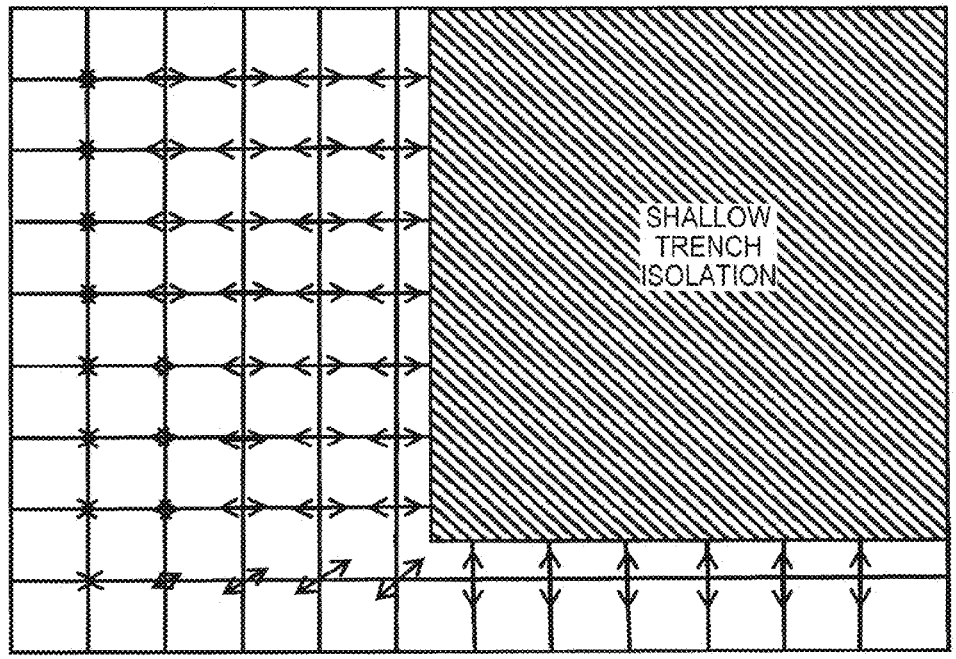
FIGS. 9A and 9B illustrate a method of determining a stress source from the magnitude and direction of principal strain at each point.
Figure 9B:
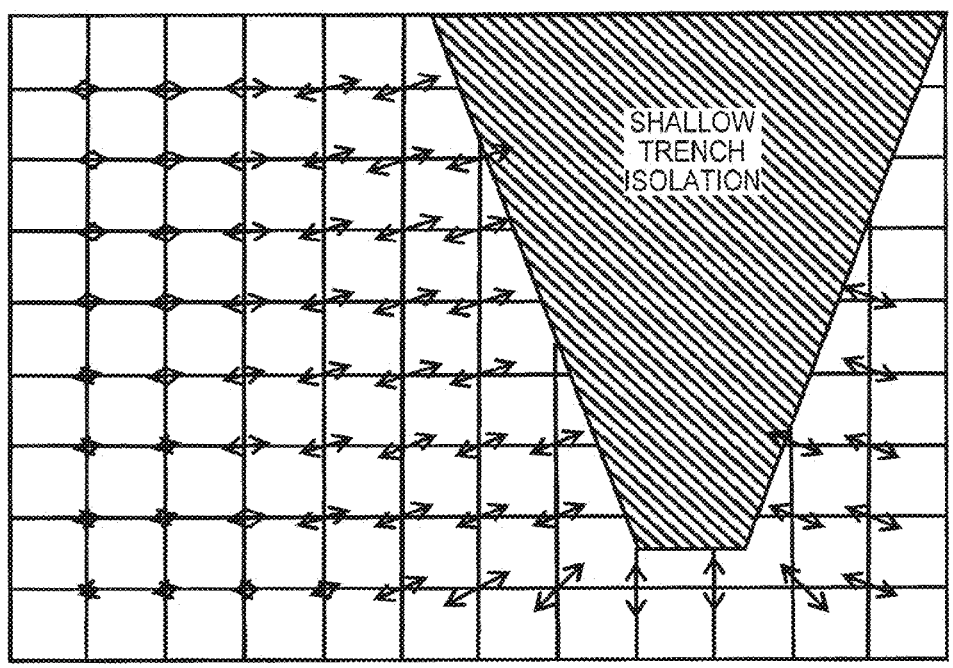

By selecting an appropriate direction $\theta$ for the strain $\epsilon_\theta$, the direction exhibiting a strain maximum level can be determined. Strain in such direction is referred to as principal strain, and the direction of the principal strain can be determined by this calculation. Namely, in expression 4, $\theta$ exhibiting a maximum strain amount $\epsilon_\theta$ is the direction of the principal strain, and the strain amount $\epsilon_\theta$ in that direction is the magnitude of the principal strain. For example, as illustrated in FIG. 9, by representing and outputting the value and the direction of principal strain at each point as the length and the direction of an arrow, respectively, a stress source can be determined (step S24 in FIG. 7).

In addition, the shear strain $\gamma_\theta$ in an arbitrary direction $\theta$ can be obtained by expression 5 (step S25 in FIG. 7). If silicon single-crystal is used, the Si (111) plane is a slip plane. For example, by obtaining a shear strain distribution image on this plane when $\theta$=54.7 degrees and −54.7 degrees, the possibility of occurrence of a crystal defect can be predicted.

$$\gamma_\theta = (\varepsilon_{xx}-\varepsilon_{yy})\sin 2\theta + \gamma_{xy}\cos 2\theta \quad \text{[expression 5]}$$

Namely, according to the second exemplary embodiment, the strain $\epsilon_\theta$ in an arbitrary direction can be obtained by using quantified strain distributions in a plurality of directions and expressions 3 and 4. Thus, from the direction exhibiting a maximum strain level $\epsilon_\theta$, the magnitude and the direction of principal strain can be obtained. In addition, from the magnitude and the direction of the principal strain, a stress source can be determined, as illustrated in FIG. 9.

In addition, the shear strain $\gamma_\theta$ in an arbitrary direction $\theta$ can be obtained based on expression 5. While the shear strain in a semiconductor device is a cause of a crystal defect, according to the second exemplary embodiment, the possibility of occurrence of a crystal defect can be predicted.

Third Exemplary Embodiment

The calculation processing apparatus 200 in the evaluation system 10 in FIG. 1 is not necessarily a dedicated calculation processing apparatus. By causing a general-purpose computer such as an EWS or a PC to execute a dedicated evaluation program stored in the storage apparatus 280, the general-purpose computer, the electron microscope 100, and peripheral apparatuses such as the sample orientation control apparatus 140, the scanning coil and lens control apparatus 180, and the electron beam detector 190 can be allowed to function as the evaluation system 10. In this case, peripheral apparatuses connectable to the general-purpose computer can be used as the display apparatus 290, the input apparatus 270, and the storage apparatus 280. In addition, by causing the general-purpose computer to execute the evaluation program stored in the storage apparatus 280, the general-purpose computer can be allowed to function as the calculation processing apparatus 200 including the control unit 210, the strain distribution image extraction unit 221, the strain quantification unit 230, and the stress analysis unit 240. Namely, according to the third exemplary embodiment, by causing a computer to execute a dedicated program, a scanning transmission electron microscope and the computer controlling the scanning transmission electron microscope and processing measurement data obtained by the scanning transmission electron microscope are allowed to function as the evaluation system and to execute the evaluation method according to the first and second exemplary embodiments.

Example 1

Figure 5A:
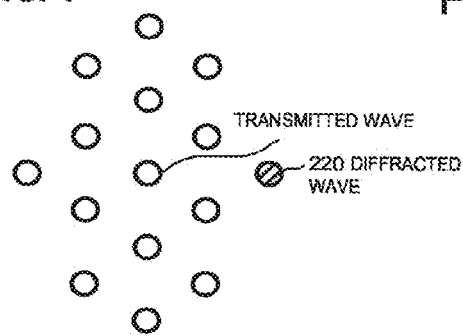
FIGS. 5A to 5C illustrate a diffracted wave, a diffracted wave intensity image, and a stress analysis diagram, respectively, used for analyzing strain in the X direction.
Figure 5D:
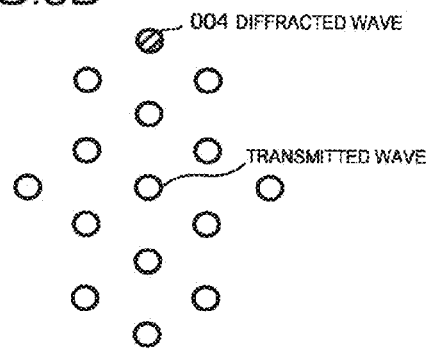
FIGS. 5D to 5F illustrate a diffracted wave, a diffracted wave intensity image, and a stress analysis diagram, respectively, used for analyzing strain in the Y direction.
Figure 5B:
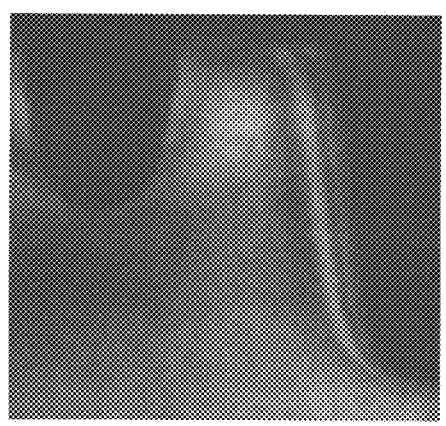
Figure 5E:
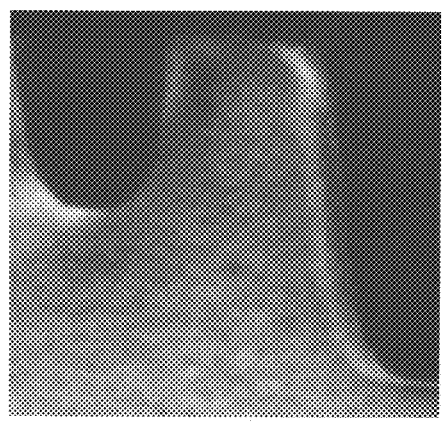
Figure 5C:
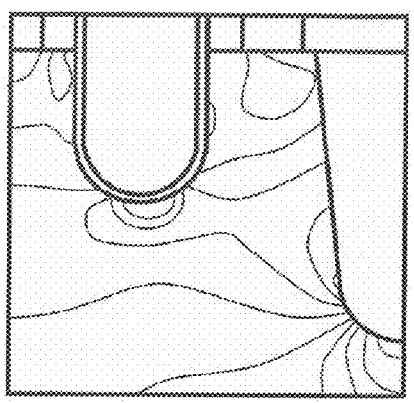
Figure 5F:
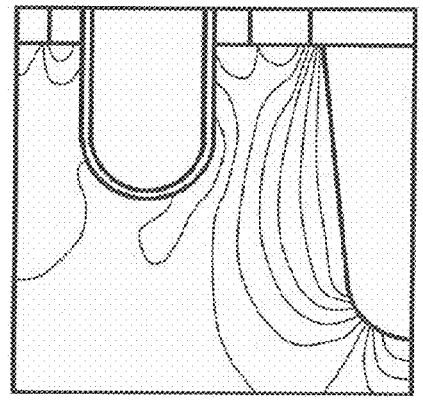

Next, example 1 will be described. In example 1, the evaluation method according to the first exemplary embodiment described with reference to FIGS. 1 to 4 is applied to a minute device having a trench gate as disclosed in Patent Document 4, for example. FIGS. 5A and 5B illustrate a diffracted wave and an intensity image thereof used for analyzing strain in the X <110> direction, respectively. FIGS. 5D and 5E illustrate a diffracted wave and an intensity image thereof used for analyzing strain in the Y <001> direction, respectively. In example 1, since the lattice strain can be displayed depending on the strain direction as illustrated in FIGS. 5B and 5E, the strain state can be grasped easily. In addition, the diffracted wave intensity images as illustrated in FIGS. 5B and 5E can be displayed by stress analysis diagrams as illustrated in FIGS. 5C and 5F. FIGS. 5C and 5F are stress analysis diagrams based on results of a process simulation executed separately from the measurement in FIGS. 5B and 5E.

As described above, according to each of the exemplary embodiments of the present disclosure, the lattice strain can be divided into directional components to be evaluated instantly, and the strain can be quantified by using the NBD method. In addition, based on the obtained results, by using a calculation processing apparatus, a shear strain distribution and a principal strain distribution, which cannot be measured by Patent Document 2 or 3 or Non-Patent Document 2, can be obtained from a strain amount at each point. As a result, the possibility of occurrence of a crystal defect can be predicted from the shear strain distribution, and a stress source can be determined by the principal strain distribution.

Fourth Exemplary Embodiment

Next, an evaluation system and an evaluation method according to a fourth exemplary embodiment will be described. In the fourth exemplary embodiment, based on the principle of the present disclosure described in the first to third exemplary embodiments and example 1, the strain direction separation performance (separation of the X-direction strain and Y-direction strain) is improved.

Figure 10B:
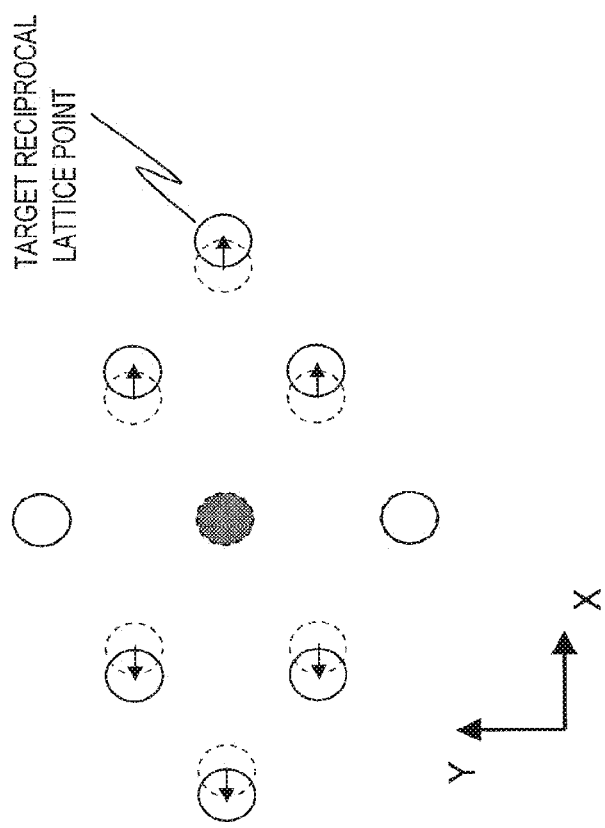
FIG. 10A illustrates the direction in which stress is caused and FIG. 10B illustrates the direction in which a reciprocal lattice point is moved when perpendicular stress is caused on a sample.
Figure 10A:
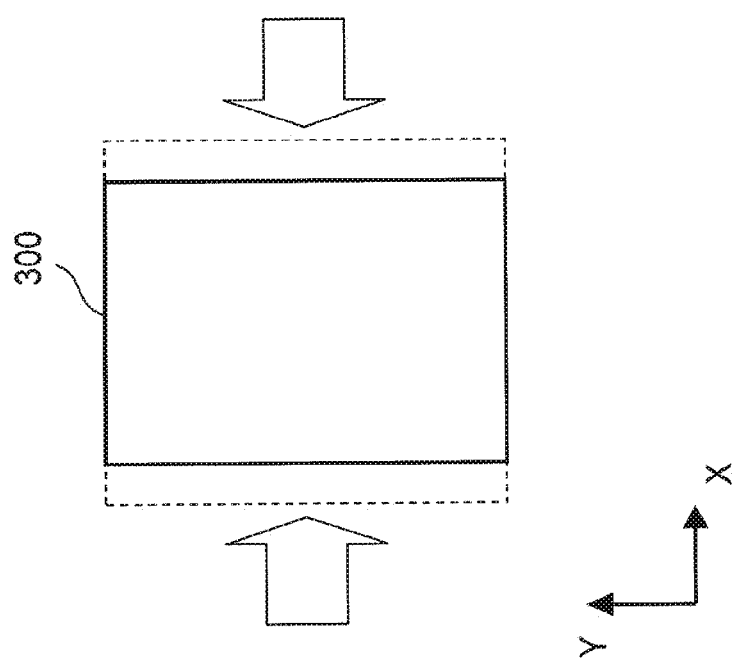

As illustrated in FIG. 10A, if stress is caused on the evaluation sample 300 in a direction perpendicular thereto (in the X direction), an ideal perpendicular-direction strain is caused. In this case, when the strain in the X-direction is evaluated, a target reciprocal lattice point only moves in the X direction, as illustrated in FIG. 10B. However, if the evaluation sample 300 is an actual LSI device, stress is caused in complex directions, as illustrated in FIG. 11A. As a result, for example, complex lattice strain including shear strain is caused. Thus, as illustrated in FIG. 11B, a target reciprocal lattice point used for evaluating a strain distribution in the X direction moves not only in the X direction but also in the Y direction. Consequently, since components such as the strain in the Y direction and shear strain are superimposed on a lattice strain distribution image obtained based on a target diffracted wave, an error is caused when the strain in the X direction is measured.

Figure 12A:
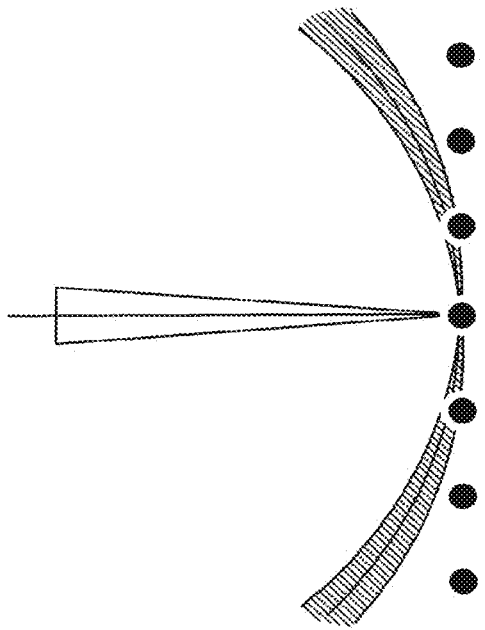
FIGS. 12A and 12B illustrate shapes of Ewald spheres formed in a reciprocal space when the electron beam incident on a sample has a large convergent angle and a small convergent angle, respectively.
Figure 12B:
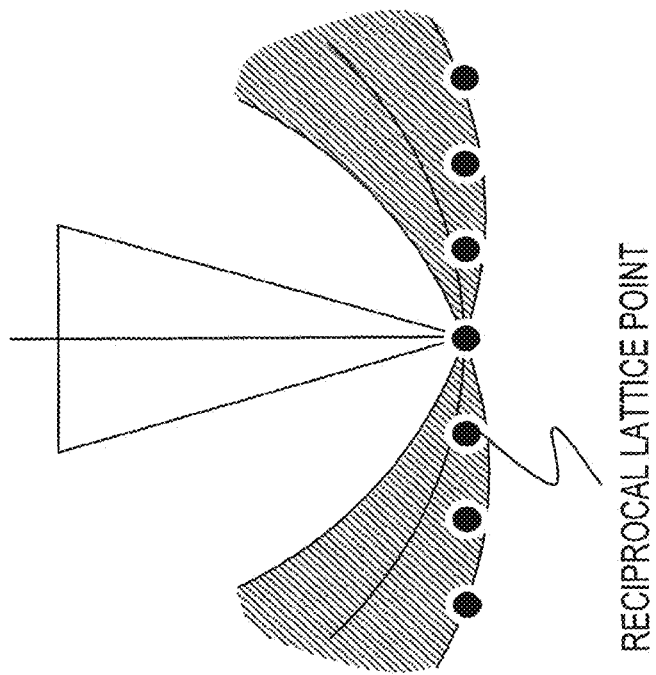

Thus, to improve the strain direction separation performance, various studies were conducted. As a result, it was found that if the electron beam incident on the crystal sample (evaluation sample 300) has greater parallelism, the strain distribution image exhibits a greater contrast. FIGS. 12A and 12B illustrate shapes of Ewald spheres formed in the reciprocal space when the electron beam incident on the crystal sample has a large convergent angle and a small convergent angle (the illumination wave focused on the crystal sample has greater parallelism), respectively. As illustrated in FIG. 12A, if the focused electron beam has a large convergent angle, since electrons are caused to be incident on the crystal sample in various directions, wider Ewald spheres are formed in the reciprocal space. As a result, since average excitation errors are made uniform, the strain contrast is weakened.

Figure 14B:
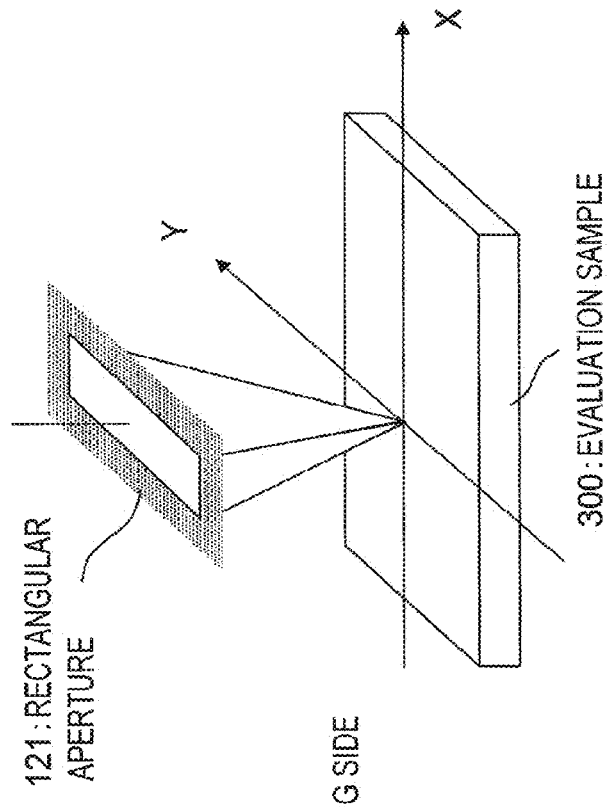
FIG. 14A is a plan view of a rectangular aperture according to the fourth exemplary embodiment and FIG. 14B is a perspective view illustrating an electron beam being incident on a sample.
Figure 14A:
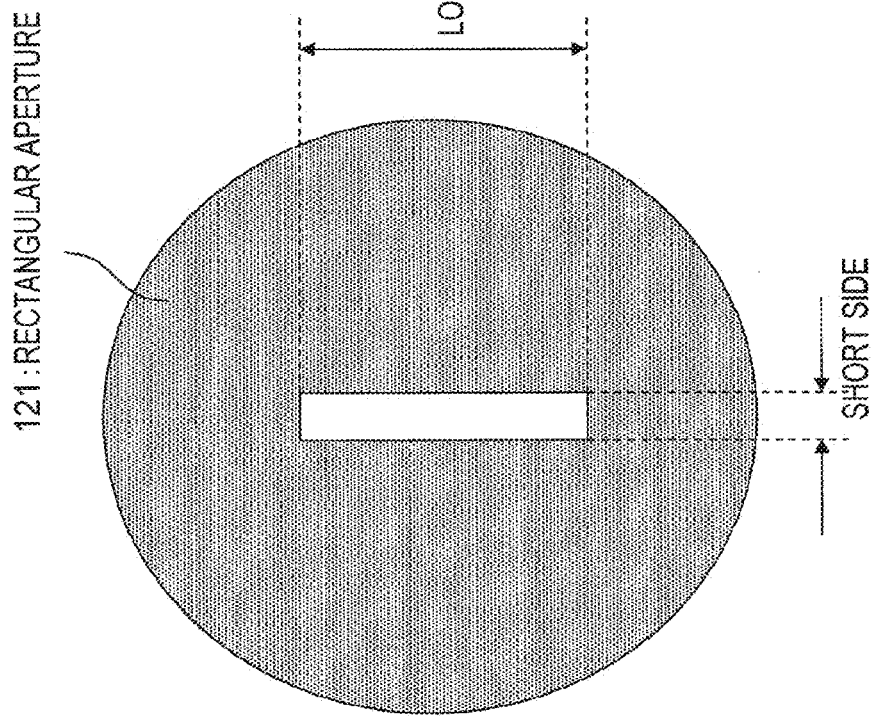

Thus, the fourth exemplary embodiment proposes a rectangular movable aperture (rectangular aperture 121) as illustrated in FIGS. 13 and 14. FIG. 13 is a block diagram illustrating an overall configuration of a system 10a for evaluating a distribution of lattice strain on crystal material according to the fourth exemplary embodiment. Elements of the evaluation system 10a in FIG. 13 that are different from those of the evaluation system 10 according to the first exemplary embodiment in FIG. 1 will be described. In the evaluation system 10a in FIG. 13, an illuminating-system lens apparatus 120a includes a rectangular aperture 121 (an illumination aperture having a rectangular opening (aperture)). The rectangular aperture 121 has a rectangular opening (aperture), as illustrated in a plan view in FIG. 14A. FIG. 14B is a perspective view illustrating an electron beam being incident on the evaluation sample 300. As illustrated in FIG. 14B, the electron beam emitted from the electron beam source 110 (see FIG. 13) is narrowed by the rectangular aperture (illumination aperture) 121 and is then focused on the evaluation sample 300 by the imaging-system lens apparatus 150 (see FIG. 13). In addition, based on the evaluation system 10a in FIG. 13, a control unit 210a included in a calculation processing apparatus 200a controls the illuminating-system lens apparatus 120a including the rectangular aperture 121.

By including this rectangular aperture 121 in the illuminating-system lens apparatus 120a, the electron beam convergent angles in the X and Y directions can be set to be asymmetrical to each other. As a result, diffraction intensity change can be obtained, focusing only the change of a reciprocal lattice point in one direction.

The fourth exemplary embodiment will be described in more detail with reference to FIGS. 15A and 15B. FIG. 15A illustrates the relationship between a cross section of the electron beam in the longitudinal direction of the rectangular aperture and reciprocal lattice points (the same as FIG. 12A). FIG. 15B illustrates an X-Y cross section of a dotted line portion in FIG. 15A (zero-order reciprocal lattice plane). Since the electron beam in the Y direction has a large convergent angle, the electron beam is incident in various angles, and wider Ewald spheres are formed. However, since the electron beam in the X direction has greater parallelism, no Ewald spheres appears on the zero-order reciprocal lattice plane. As a result, while small excitation errors are exhibited in the movement direction of the reciprocal lattice points (in the Y direction), large excitation errors are exhibited in the other direction. Namely, since the electron beam has a large convergent angle in the Y direction, even if, of the focused electron beam, the electron beam focused in one direction exhibits small excitation errors because of movement of the reciprocal lattice points in the Y direction, the electron beam focused in the other direction exhibits large excitation errors. Therefore, the diffraction intensity is not changed. However, since the movement in the X direction is due to the electron beam having greater parallelism, the diffraction intensity is changed. As a result, it is possible to obtain a lattice strain distribution having reduced strain errors in the short-side direction of the rectangular aperture.

In this example, the rectangular aperture 121 is set so that the long and short side thereof are perpendicular and parallel to the direction of a certain diffracted wave detected with respect to a transmitted wave, respectively. For example, in FIG. 3B, when detecting the diffracted wave 220 diffracted in the X direction with respect to the transmitted wave, the direction of the rectangular aperture 121 is adjusted so that the long and short sides thereof are parallel to the Y-axis and the X-axis, respectively. Similarly, in FIG. 3B, when detecting the diffracted wave 002 or 004 diffracted in the Y direction with respect to the transmitted wave, the direction of the rectangular aperture 121 is adjusted so that the long and short sides thereof are parallel to the X-axis and Y-axis, respectively. In addition, while a certain advantageous effect can be obtained as long as the long side is longer than the short side; however, to reduce strain errors, it is desirable that the ratio of the long side to the short side be 4:1 or greater.

FIG. 16 illustrates a rectangular aperture 121 having a plurality of rectangular apertures on a single metal plate. This rectangular aperture 121 in FIG. 16 includes an X-direction evaluation rectangular aperture 401, a Y-direction evaluation rectangular aperture 402, and a 111-direction evaluation rectangular aperture 403. In this way, strain distribution images having greater strain separation performance in the X, Y, and 111 directions can be obtained. Generally, an illuminating lens system includes a plurality of electron beam lenses, a deflector, and an aperture. Thus, by using an upstream lens and an aperture, a rectangular aperture having the long side thereof in an arbitrary direction can be selected.

FIG. 17 is a flow chart illustrating a method of evaluating a distribution of lattice strain on crystal material according to the fourth exemplary embodiment. When compared with the flow chart in FIG. 2 illustrating the evaluation method according to the first exemplary embodiment, the flow chart in FIG. 17 includes step S31 before the detector 190 captures a certain diffracted wave in step S3. In step S31, the rectangular aperture 121 is adjusted, based on the certain diffracted wave to be detected. The adjustment of the rectangular aperture 121 (step S31) may be executed at an arbitrary timing, as long as the adjustment is executed before the detector 190 captures a certain diffracted wave in step S3. For example, if the rectangular aperture 121 is a rectangular aperture including a plurality of apertures (openings) as illustrated in FIG. 16, when an upstream lens of the illuminating-system lens apparatus 120a is controlled, an aperture matching a certain diffracted wave to be detected can be selected. Alternatively, the relative direction of the rectangular aperture 121 and the evaluation sample 300 on the XY plane may be adjusted by rotating the rectangular aperture 121 and/or the evaluation sample 300 on the XY plane, for example. Other steps similar to those according to the first exemplary embodiment are denoted by the same reference characters, and repetitive descriptions will be omitted.

Needless to say, the above fourth exemplary embodiment can be combined with the analysis of a principal strain distribution and a shear strain distribution in an arbitrary direction according to the second exemplary embodiment. According to the fourth exemplary embodiment, the strain direction separation performance can be improved. Thus, it is expected that a principal strain distribution or a shear strain distribution in an arbitrary direction can be analyzed more accurately. In addition, the fourth exemplary embodiment can be implemented by causing a general-purpose computer such as an EWS or a PC described in the third exemplary embodiment to execute a dedicated evaluation program. The computer program caused to function as the evaluation system according to the fourth exemplary embodiment includes a program for controlling the relative direction of the opening (aperture) of the rectangular aperture 121 with respect to the evaluation sample 300 in the electron microscope 100a.

According to each of aspects, modes, or exemplary embodiments of the present disclosure, a strain distribution image is obtained by selecting a certain diffracted wave. Thus, by evaluating a selected diffracted wave, a strain distribution image per direction can be obtained. In addition, the possibility of occurrence of a crystal defect can be predicted or a stress source can be determined, based on such strain distribution image per direction.

Modifications and adjustments of the exemplary embodiments and examples are possible within the scope of the overall disclosure (including the claims and the drawings) of the present invention and based on the basic technical concept of the present invention. Various combinations and selections of various disclosed elements (including the elements in the claims, exemplary embodiments, drawings, etc.) are possible within the scope of the claims of the present invention. That is, the present invention of course includes various variations and modifications that could be made by those skilled in the art according to the overall disclosure including the claims and the drawings and based on the technical concept.

What is claimed is:

1. A method of evaluating a distribution of lattice strain on crystal material, the method comprising:
   illuminating a sample having a crystal structure with an electron beam in a zone axis direction (termed as "illuminating step") and selectively detecting a certain diffracted wave diffracted in a certain direction among a plurality of diffracted waves diffracted by the sample (termed as "selectively detecting step"); and
   repeating said illuminating step and said selectively detecting step while scanning the sample, and obtaining a strain distribution image in a direction corresponding to the certain diffracted wave from diffraction intensity at each point of the sample (termed as "strain distribution image obtaining step").

2. The method according to claim 1, further comprising steps of:
   repeating said strain distribution image obtaining step for each of a plurality of diffracted waves diffracted in directions different from each other and obtaining strain distribution images in directions corresponding to the directions of the diffracted waves, based on the diffracted waves diffracted in directions different from each other; and
   executing stress analysis on the sample, based on the strain distribution images in the plurality of directions.

3. The method according to claim 2, further comprising:
   quantifying the magnitude of strain of the strain distribution image.

4. The method according to claim 3;
   wherein executing the stress analysis further comprises:
   calculating shear strain in a certain direction, based on strain measurement results in a plurality of directions; and
   calculating the magnitude and direction of principal strain, based on strain measurement results in a plurality of directions and the calculated shear strain in a certain direction.

5. The method according to claim 3;
   wherein executing the stress analysis further comprises:
   calculating shear strain in a certain direction, based on strain measurement results in a plurality of directions; and
   obtaining shear strain in an arbitrary direction, based on the strain measurement results in a plurality of directions and the calculated shear strain in a certain directions.

6. The method according to claim 1;
   wherein the sample is a TEM sample which is formed by thinning material having a crystal structure to have a uniform thickness, and the certain diffracted wave is obtained by forward scattering.

7. The method according to claim 1;
   wherein, in said selectively detecting step, the electron beam with which the sample is illuminated is narrowed to a rectangle having long and short sides perpendicular and parallel to a direction in which the certain diffracted wave is diffracted with respect to the transmitted wave, respectively, and the narrowed electron beam is focused on the sample.

8. A system of evaluating a distribution of lattice strain on crystal material, the system comprising:
   a scanning transmission electron microscope that illuminates a sample with an electron beam, scans the sample, and detects a diffracted wave transmitted or diffracted by the sample; and a strain distribution image extraction unit that selects a certain diffracted wave among diffracted waves transmitted or diffracted by the sample, and obtains a strain distribution image.

9. The system according to claim 8, further comprising:
a strain quantification unit that quantifies strain intensity of the strain distribution image.

10. The system according to claim 8, further comprising:
a stress analysis unit;
wherein the strain distribution image extraction unit obtains strain distribution images in a plurality of directions each corresponding to the direction of one of a plurality of diffracted waves diffracted in directions different from each other; and
wherein the stress analysis unit executes stress analysis on the sample, based on the strain distribution images in a plurality of direction obtained by the strain distribution image extraction unit.

11. The system according to claim 10;
wherein the stress analysis unit is configured to execute processes of:
calculating shear strain in a certain direction, based on the strain distribution images in a plurality of directions; and
calculating the magnitude and direction of principal strain, based on the strain distribution images in a plurality of directions and the calculated shear strain in a certain direction.

12. The system according to claim 10;
wherein the stress analysis unit is configured to execute processes of:
calculating shear strain in a certain direction, based on the strain distribution images in a plurality of directions; and
calculating shear strain in an arbitrary direction, based on the strain distribution images in a plurality of directions and the calculated shear strain in a certain direction.

13. The system according to claim 8;
wherein the scanning transmission electron microscope further comprises a sample orientation control apparatus that adjusts crystal orientation of the sample with respect to the direction of the incident electron beam.

14. The system according to claim 8, further comprising: a display apparatus that displays evaluation results including the strain distribution image.

15. The system according to claim 8;
wherein the scanning transmission electron microscope comprises an illumination aperture having a rectangular opening to narrow the electron beam and illuminate the sample with the narrowed electron beam; and
wherein the rectangular opening of the illumination aperture can be set so that the long and short sides thereof are perpendicular and parallel to a direction in which the certain diffracted wave is diffracted with respect to the transmitted wave, respectively.

16. The system according to claim 15;
wherein the illumination aperture comprises a plurality of rectangular openings, each of which has long and short sides in different directions; and
wherein, in accordance with a direction in which the certain diffracted wave is diffracted, an opening is selectable from the plurality of openings as an aperture to illuminate the sample with the electron beam with the selected opening.

17. A non-transitory computer-readable recording medium storing a computer program used in an evaluation system comprising a scanning transmission electron microscope and a computer that controls the scanning transmission electron microscope and processes measurement data obtained by the scanning transmission electron microscope, the computer program causing the computer to execute processes of:
controlling the scanning transmission electron microscope so that a sample having a crystal structure is illuminated with an electron beam and a diffracted wave transmitted or diffracted by the sample is detected; and
scanning the sample, selecting a certain diffracted wave among diffracted waves transmitted or diffracted by the sample, and obtaining a strain distribution image.

18. The non-transitory computer-readable recording medium according to claim 17;
wherein said scanning transmission electron microscope comprises an illumination aperture having a rectangular opening whose direction is changeable; and
wherein said process of controlling the scanning transmission electron microscope includes controlling of the direction of the rectangular opening of the illumination aperture in accordance with a direction in which the certain diffracted wave is diffracted with respect to the transmitted light.

* * * * *